United States Patent [19]
Carroll

[11] Patent Number: 6,019,103
[45] Date of Patent: Feb. 1, 2000

[54] DISPOSABLE SANITARY EYE PROTECTOR

[76] Inventor: Lynnette Carroll, 320 Bedford Rd., Las Vegas, Nev. 89107

[21] Appl. No.: 09/031,377

[22] Filed: Feb. 26, 1998

[51] Int. Cl.$^7$ .................................................. A61F 9/00
[52] U.S. Cl. ............................................. 128/858; 2/426
[58] Field of Search ................................... 128/857, 858; 602/74; 2/15, 426–428, 431, 434, 440, 441

[56] References Cited

U.S. PATENT DOCUMENTS

| | | | |
|---|---|---|---|
| 4,122,847 | 10/1978 | Craig ......................................... | 2/15 X |
| 4,393,080 | 7/1983 | Pawelchak et al. .................. | 602/52 X |
| 4,547,909 | 10/1985 | Bell ............................................ | 2/431 |
| 4,797,956 | 1/1989 | Boyce ........................................ | 2/431 |
| 4,944,294 | 7/1990 | Borek, Jr. ........................... | 128/206.19 |
| 5,383,450 | 1/1995 | Hubbard et al. ................... | 128/206.23 |
| 5,406,944 | 4/1995 | Gazzara ............................. | 128/206.15 |
| 5,419,913 | 5/1995 | Podell et al. ......................... | 602/77 X |
| 5,425,380 | 6/1995 | Hudson et al. ......................... | 128/858 |
| 5,446,925 | 9/1995 | Baker et al. .................................... | 2/9 |
| 5,596,985 | 1/1997 | Collier ............................... | 128/206.19 |
| 5,700,238 | 12/1997 | Hyson ...................................... | 602/74 |

Primary Examiner—Richard J. Apley
Assistant Examiner—Denise Pothier
Attorney, Agent, or Firm—Joseph N. Breaux

[57] ABSTRACT

A disposable sanitary eye protector device that includes a molded, flexible plastic, face shield portion having two eye protector openings and nose receiving cut-out; two domed shaped clear plastic eye protectors, one installed through each of the eye protector openings of the face shield portion; and an elastic securing cord having the cord ends thereof secured to the face shield portion to form a head encircling loop. The molded, flexible plastic, face shield portion is molded to the general contours of the eye and nose area of a wearer. Each of the two domed shaped, clear plastic eye protectors includes a transparent domed portion having an eye receiving cavity formed therein that is accessible through an eye insertion opening defined by an attachment ridge formed around the entire perimeter of the eye protector. In a preferred embodiment, a back surface of the face shield portion is coated with a restickable adhesive layer and a peel off cover to ensure the back surface of the face shield portion slightly adheres to the face of the wearer during user. The restickable adhesive layer may be impregnated with an antiseptic agent to kill contagions, such as bacteria and viruses, that may accidentally contact the wearer's face.

1 Claim, 2 Drawing Sheets

__DISPOSABLE SANITARY EYE PROTECTOR__

TECHNICAL FIELD

The present invention relates to protector devices and more particularly to a disposable sanitary eye protector for protecting the eye and upper face area of a wearer from biological hazards such as those generated during dental and other surgical procedures that includes a molded, flexible plastic, face shield portion having two eye protector openings and nose receiving cut-out; two domed shaped, clear plastic eye protectors, one installed through each of the eye protector openings of the face shield portion; and an elastic securing cord having the cord ends thereof secured to the face shield portion to form a head encircling loop; the molded, flexible plastic, face shield portion being molded to the general contours of the eye and nose area of a wearer; each of the two domed shaped, clear plastic eye protectors including a transparent domed portion having an eye receiving cavity formed therein that is accessible through an eye insertion opening defined by an attachment ridge formed around the entire perimeter of the eye protector; the back surface of the face shield portion being optionally coated with a restickable adhesive layer to ensure the back surface of the face shield portion slightly adheres to the face of the wearer; the optional restickable adhesive layer being covered by a peel off adhesive layer cover that is removable by the user prior to use, preferably impregnated with an antiseptic agent to kill contagions, such as bacteria and viruses, that may accidentally contact the wearer's face.

BACKGROUND ART

Many diseases are transmitted from one person to another through contact with bodily fluids, such as spattered blood and other tissues generated during dental procedures and the like. One of the easiest areas for this contact to occur is the eye area. It would be a benefit, therefore, to have an eye protector that could be placed over the eyes to prevent splattering of blood and tissue into the eyes and onto the face area surrounding the eyes during dental and other surgical procedures. Because contagions can also be smeared into the eyes after initially contacting the hands and fingers, it would be a further benefit to have an eye protector that included a face shield to prevent the wearer from scratching or touching the face area surrounding the eyes until the wearer's hands and fingers had been thoroughly cleaned and disinfected. It would of course be a still further benefit to have an eye protector that included an antiseptic mechanism or agent for killing contagions on the face area surrounding the eyes of the wearer before the contagions could enter one of the eyes.

GENERAL SUMMARY DISCUSSION OF INVENTION

It is thus an object of the invention to provide a disposable sanitary eye protector.

It is a further object of the invention to provide a disposable sanitary eye protector that includes a face shield for preventing splattering of bodily fluids and tissues onto the area of the face surrounding the eyes.

It is a still further object of the invention to provide a disposable sanitary eye protector that includes a face shield having a restickable adhesive mechanism for adhering the face shield to the face to prevent the wearer from inadvertently scratching the area of the face surrounding the eyes until his/her hands have been cleaned and disinfected following a surgical procedure.

It is a still further object of the invention to provide a disposable sanitary eye protector that includes a face shield having an antiseptic mechanism or agent for killing contagions on the face area surrounding the eyes of the wearer before the contagions can enter one of the wearer's eyes.

That accomplishes some or all of the above objects in combination.

Accordingly, a disposable sanitary eye protector is provided. The disposable sanitary eye protector includes a molded, flexible plastic, face shield portion having two eye protector openings and nose receiving cut-out; two domed shaped, clear plastic eye protectors, one installed through each of the eye protector openings of the face shield portion; and an elastic securing cord having the cord ends thereof secured to the face shield portion to form a head encircling loop. The molded, flexible plastic, face shield portion is molded to the general contours of the eye and nose area of a wearer. Each of the two domed shaped, clear plastic eye protectors includes a transparent domed portion having an eye receiving cavity formed therein that is accessible through an eye insertion opening defined by an attachment ridge formed around the entire perimeter of the eye protector. In a preferred embodiment a back surface of the face shield portion is coated with a restickable adhesive layer to ensure the back surface of the face shield portion slightly adheres to the face of the wearer during use. When the restickable adhesive layer is used, the eye protector also preferably includes a peel off adhesive layer cover that is removable by the user prior to use. In another preferred embodiment, the back surface of the face shield portion is coated with a restickable adhesive layer that is impregnated with an antiseptic agent to kill contagions, such as bacteria and viruses, that may accidentally contact the wearer's face.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

EXEMPLARY MODE FOR CARRYING OUT THE INVENTION

Figure 1:
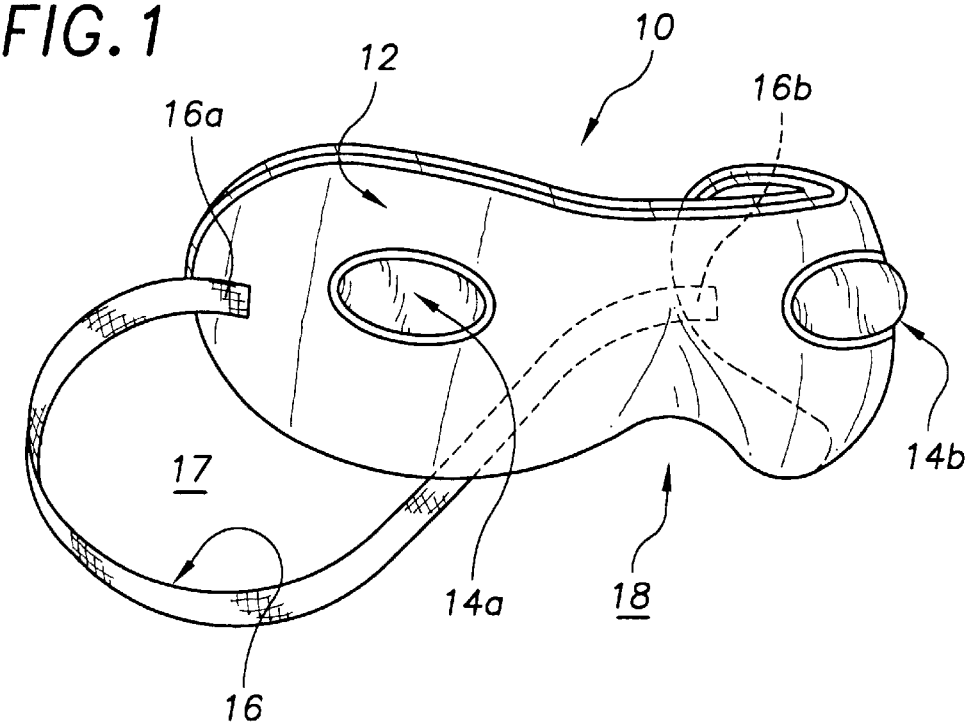
FIG. 1 is a perspective view of a first exemplary embodiment of the disposable sanitary eye protector of the present invention showing the molded, flexible plastic, face shield portion including the two eye protector openings and the nose receiving cut-out; the two domed shaped, clear plastic eye protectors installed in the eye protector openings of the face shield portion; and the elastic securing cord secured to the face shield portion.

FIG. 1 shows a first exemplary embodiment of the disposable sanitary eye protector of the present invention generally designated by the numeral 10. In this embodiment, disposable sanitary eye protector 10 includes a molded, flexible plastic, face shield portion, generally designated 12; two domed shaped, clear plastic eye protectors, generally designated 14*a*,14*b*, respectively; and an elastic securing cord, generally designated 16, having cord ends 16*a*,16*b* secured to face shield portion 12 to form a head encircling loop 17. Face shield portion 12 is constructed of vinyl and is molded to the general contours of the eye and nose area of a wearer including a nose receiving notch 18.

Figure 2:
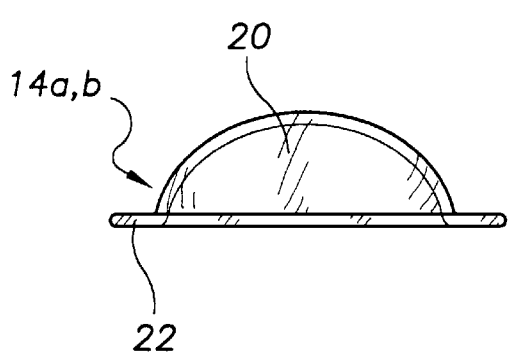
FIG. 2 is a side view of one of the domed shaped, clear plastic eye protectors showing the transparent domed portion and the attachment ridge.
Figure 3:
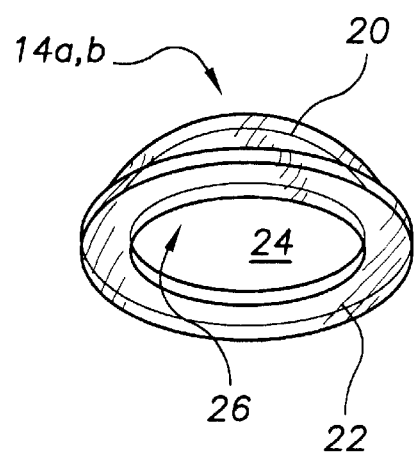
FIG. 3 is an underside perspective view of the domed shaped, clear plastic eye protector of FIG. 2 showing the eye receiving cavity and the eye insertion opening defined by the attachment ridge.

With reference to FIG. 2, each of the domed, shaped clear plastic eye protectors 14*a, b* is molded of clear plastic and includes a transparent domed portion 20 and a circumferential attachment ridge 22. Referring now to FIG. 3, an eye receiving cavity 24 is formed into the domed portion 20 of each plastic eye protector 14*a, b* that is accessible through an oval shaped eye insertion opening 26 that is defined by attachment ridge 22. Eye receiving cavity 24 is sized to receive the lashes and lid of the wearer's eye.

Figure 4:
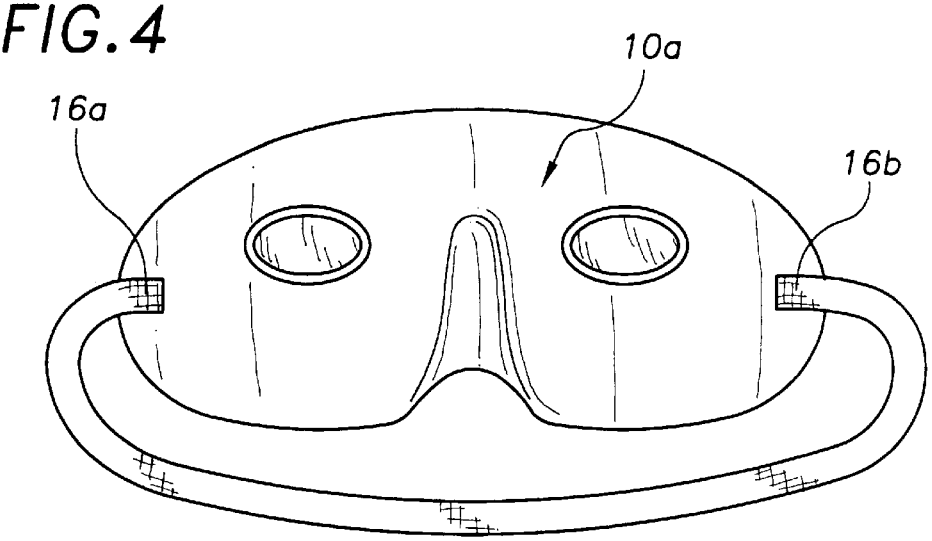
FIG. 4 is a front plan view of a second exemplary embodiment of the disposable sanitary eye protector of the present invention.
Figure 5:
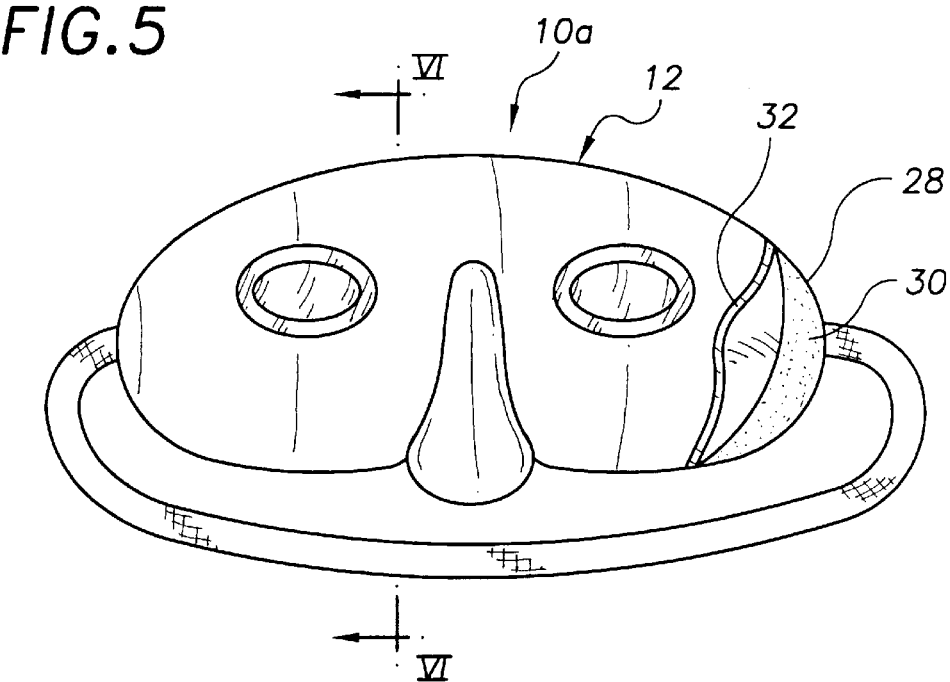
FIG. 5 is a back plan view of the second exemplary disposable sanitary eye protector of FIG. 4 showing the optional peel off adhesive layer cover partially peeled back to reveal the optional layer of restickable adhesive deposited onto the back surface of the face shield portion.
Figure 6:
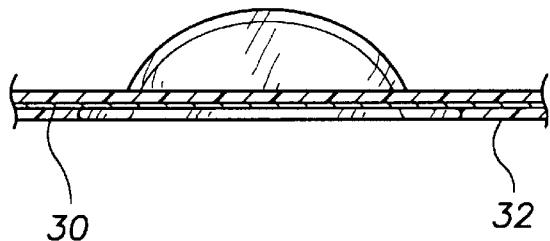
FIG. 6 is a cross sectional view of the second exemplary disposable sanitary eye protector of FIG. 5 showing the flexible plastic face shield layer, the optional restickable adhesive layer, the optional peel off adhesive layer cover and the domed shaped, clear plastic eye protector including the transparent domed portion and the attachment ridge.

FIG. 4 shows a second exemplary embodiment of the disposable sanitary eye protector of the present invention, generally designated by the designation 10*a*. Disposable sanitary eye protector 10*a* is identical in construction to disposable sanitary eye protector 10 (FIG. 1) except that, with reference now to FIG. 2, a back surface 28 of face shield portion 12 is covered with a restickable adhesive layer 30 that, in turn, is covered by a peel off cover 32. With reference to FIG. 5, in this embodiment, restickable adhesive layer 30 is impregnated with an alcohol base antiseptic agent prior to placing peel off cover 32 thereover. Referring back to FIG. 5, in use, a user can wear disposable sanitary eye protector 10*a* with peel off cover 32 in place or removed. When peel off cover 32 is removed, restickable adhesive layer 30 provides a tacky coating that holds face shield portion 12 on the face of the wearer but does not cause discomfort when face shield portion 12 is removed.

It can be seen from the preceding description that a disposable sanitary eye protector has been provided that includes a face shield for preventing splattering of bodily fluids and tissues onto the area of the face surrounding the eyes; that includes a face shield having a restickable adhesive layer for adhering the face shield to the face to prevent the wearer from inadvertently scratching the area of the face surrounding the eyes until his/her hands have been cleaned and disinfected following a surgical procedure; and that includes a face shield having an antiseptic mechanism or agent for killing contagions on the face area surrounding the eyes of the wearer before the contagions can 20 enter one of the wearer's eyes.

It is noted that the embodiment of the disposable sanitary eye protector described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A disposable sanitary eye protector comprising:
   a molded, flexible plastic, face shield portion having two eye protector openings and nose receiving cut-out;
   two domed shaped, clear plastic eye protectors, one installed through each of the eye protector openings of the face shield portion; and
   an elastic securing cord having the cord ends thereof secured to the face shield portion to form a head encircling loop;
   said molded, flexible plastic, face shield portion being molded to the general contours of the eye and nose area of a wearer;
   each of said two domed shaped, clear plastic eye protectors including a transparent domed portion having an eye receiving cavity formed therein that is accessible through an eye insertion opening defined by an attachment ridge formed around the entire perimeter of the eye protector;
   said face shield portion including a back surface that is coated with a restickable adhesive layer impregnated with an antiseptic agent;
   said antiseptic agent being alcohol.

\* \* \* \* \*